United States Patent
Huang et al.

(10) Patent No.: US 10,107,782 B2
(45) Date of Patent: Oct. 23, 2018

(54) METHOD TO PERFORM LIMITED TWO DIMENSIONAL SEPARATION OF PROTEINS AND OTHER BIOLOGICALS

(75) Inventors: Tiemin Huang, Waterloo (CA); Jiaqi Wu, Woodbridge (CA)

(73) Assignee: ProteinSimple, Santa Clara, CA (US)

( * ) Notice: Subject to any disclaimer, the term of this patent is extended or adjusted under 35 U.S.C. 154(b) by 119 days.

(21) Appl. No.: 12/358,724

(22) Filed: Jan. 23, 2009

(65) Prior Publication Data
US 2009/0194419 A1   Aug. 6, 2009

Related U.S. Application Data

(60) Provisional application No. 61/023,492, filed on Jan. 25, 2008.

(51) Int. Cl.
G01N 27/447  (2006.01)
C07K 1/28  (2006.01)
C07K 1/36  (2006.01)

(52) U.S. Cl.
CPC ....... *G01N 27/44795* (2013.01); *C07K 1/285* (2013.01); *C07K 1/36* (2013.01); *G01N 27/44721* (2013.01); *G01N 27/44773* (2013.01)

(58) Field of Classification Search
CPC ....... G01N 27/44721; G01N 27/44773; G01N 27/44795
USPC .................................................. 204/451, 603
See application file for complete search history.

(56) References Cited

U.S. PATENT DOCUMENTS

| | | |
|---|---|---|
| 1,015,891 A | 1/1912 | Ikeda et al. |
| 4,921,790 A | 5/1990 | O'Brien |
| 5,096,807 A | 3/1992 | Leaback |
| 5,106,951 A | 4/1992 | Morgan, Jr. et al. |
| 5,110,434 A | 5/1992 | Zhu et al. |
| 5,180,475 A | 1/1993 | Young et al. |
| 5,228,960 A | 7/1993 | Liu et al. |
| 5,244,813 A | 9/1993 | Walt et al. |
| 5,264,101 A | 11/1993 | Demorest et al. |
| 5,302,264 A * | 4/1994 | Welch et al. ........... 204/452 |
| 5,348,633 A | 9/1994 | Karger et al. |
| 5,376,249 A | 12/1994 | Afeyan et al. |
| 5,468,359 A | 11/1995 | Pawliszyn |
| 5,482,867 A | 1/1996 | Barrett et al. |

(Continued)

FOREIGN PATENT DOCUMENTS

EP  0805215  11/1997
JP  05-172815 A  7/1993

(Continued)

OTHER PUBLICATIONS

Canadian Office Action for corresponding Canadian Patent Application No. 2,712,213, dated Mar. 22, 2016.

(Continued)

*Primary Examiner* — Louis J Rufo

(57) ABSTRACT

A method and apparatus are provided for performing capillary isoelectric focusing followed by mobilization of the focused zones by induced hydrodynamic flow or chemical mobilization. These two dimensions of separation are integrated with real-time whole-channel electrophoresis detection and automatic sample injection to achieve a separation resolution superior to that obtainable using known orthogonal capillary two dimensional arrangements.

20 Claims, 6 Drawing Sheets

(56) References Cited

U.S. PATENT DOCUMENTS

| | | | |
|---|---|---|---|
| 5,505,831 A * | 4/1996 | Liao | G01N 27/44795 204/451 |
| 5,614,073 A | 3/1997 | Bobbitt et al. | |
| 5,627,643 A | 5/1997 | Birnbaum et al. | |
| 5,630,924 A | 5/1997 | Fuchs et al. | |
| 5,633,129 A | 5/1997 | Karger et al. | |
| 5,759,770 A | 6/1998 | Guertler et al. | |
| 5,766,435 A * | 6/1998 | Liao | G01N 27/44795 204/451 |
| 5,804,384 A | 9/1998 | Mueller et al. | |
| 5,840,503 A | 11/1998 | Beausang et al. | |
| 5,858,188 A | 1/1999 | Soane et al. | |
| 5,882,864 A | 3/1999 | An et al. | |
| 5,932,080 A | 8/1999 | Likuski | |
| 5,963,456 A | 10/1999 | Klein et al. | |
| 5,976,336 A | 11/1999 | Dubrow et al. | |
| 5,976,896 A | 11/1999 | Kumar et al. | |
| 5,985,121 A | 11/1999 | Wu et al. | |
| 6,037,138 A | 3/2000 | Moses et al. | |
| 6,054,032 A | 4/2000 | Haddad et al. | |
| 6,100,045 A | 8/2000 | Van Es | |
| 6,107,038 A | 8/2000 | Choudhary et al. | |
| 6,139,797 A | 10/2000 | Suzuki et al. | |
| 6,208,941 B1 | 3/2001 | Marks | |
| 6,375,817 B1 | 4/2002 | Taylor et al. | |
| 6,475,364 B1 | 11/2002 | Dubrow et al. | |
| 6,818,112 B2 | 11/2004 | Schneider et al. | |
| 6,849,396 B2 * | 2/2005 | Schneider | 435/4 |
| 6,852,206 B2 * | 2/2005 | Pawliszyn et al. | 204/610 |
| 7,316,770 B2 | 1/2008 | Inaba et al. | |
| 7,935,489 B2 | 5/2011 | O'Neill et al. | |
| 8,021,611 B2 | 9/2011 | Roach et al. | |
| 8,945,361 B2 | 2/2015 | Gentalen et al. | |
| 9,377,440 B2 | 6/2016 | Wu et al. | |
| 2002/0029968 A1 | 3/2002 | Tan et al. | |
| 2002/0071847 A1 | 6/2002 | Sadziene et al. | |
| 2002/0110900 A1 | 8/2002 | Jovanovich et al. | |
| 2002/0115740 A1 | 8/2002 | Beuhler et al. | |
| 2003/0078314 A1 | 4/2003 | Johnson et al. | |
| 2003/0116436 A1 | 6/2003 | Amirkhanian et al. | |
| 2003/0128043 A1 | 7/2003 | Zeltz et al. | |
| 2003/0148532 A1 | 8/2003 | Edwards et al. | |
| 2004/0166546 A1 | 8/2004 | Warmington et al. | |
| 2004/0168917 A1 * | 9/2004 | Tabuchi et al. | 204/451 |
| 2006/0057576 A1 | 3/2006 | Paszkowski et al. | |
| 2006/0127275 A1 | 6/2006 | Holl et al. | |
| 2006/0254914 A1 * | 11/2006 | Biron et al. | 204/451 |
| 2008/0017512 A1 | 1/2008 | Bordunov et al. | |
| 2008/0035484 A1 | 2/2008 | Wu et al. | |
| 2008/0149484 A1 * | 6/2008 | Tolley | G01N 33/561 204/451 |
| 2009/0023156 A1 | 1/2009 | Voss et al. | |
| 2010/0155241 A1 * | 6/2010 | Ross et al. | 204/451 |
| 2010/0307920 A1 * | 12/2010 | Sivan | G01N 27/44743 204/548 |
| 2011/0011740 A1 | 1/2011 | Roach et al. | |
| 2011/0139622 A1 | 6/2011 | Tolley et al. | |
| 2012/0274760 A1 | 11/2012 | King et al. | |
| 2012/0322686 A1 | 12/2012 | Lyon et al. | |
| 2013/0280815 A1 | 10/2013 | Wu | |
| 2015/0090591 A1 | 4/2015 | Yang et al. | |
| 2015/0093757 A1 | 4/2015 | Gavin | |

FOREIGN PATENT DOCUMENTS

| | | |
|---|---|---|
| WO | WO 99/63408 | 12/1999 |
| WO | WO 2001/055721 | 8/2001 |
| WO | WO 2003/100086 | 12/2003 |

OTHER PUBLICATIONS

Shimura, K. et al., "Fluorescence-Labeled Peptide pI Markers for Capillary Isoelectric Focusing," Anal. Chem., 74:1046-1053 (2002).

Office Action for Canadian Patent Application No. 2,712,213, dated Mar. 19, 2018, 4 pages.

Biorad Laboratories Inc., "A Guide to Polyacrylamide Gel Electrophoresis and Detection BEGIN," Jan. 1, 2011, Hercules, CA, Retrieved from the Internet: URL: http://www.bio-rad.com/webroot/web/pdf/lsr/literature/Bulletin_6040A.pdf [retrieved Mar. 3, 2015].

Bossi, A. et al., "Capillary Electrophoresis Coupled to Biosensor Detection," J. Chromatography A, 892:143-153 (2000).

Chandler, J. P., "Purification and characterization of antibodies," pp. 125-155 (2006).

Chang, W., et al., "Enhanced Resolution Achieved with Electroosmotic Flow Control in Capillary Isoelectric Focusing with Dynamic Coatings," Am. Biotechnology. Lab. (2005).

Chen, X. et al., "Charge-based analysis of antibodies with engineered cysteines From multiple peaks to a single main peak," MABS, Landes Bioscience, 1(6):563-571 (2009).

Khandurina, J. et al., "Micromachined capillary cross-connector for high-precision fraction collection," Journal of Chromatography A, 979(1-2):105-113 (2002).

Khandurina, J. et al., "Micropreparative fraction collection in microfluidic devices," Anal. Chem., 74(7):1737-1740 (2002).

Kaniansky, D. et al., "Capillary electrophoresis Separations on a planar chip with the column-coupling configuration of the separation channels," Anal. Chem., 72(15):3596-3604 (2000).

Liu, H. et al., "On-line combination of capillary isoelectric focusing and capillary non-gel sieving electrophoresis using a hollow-fiber membrane interface: a novel two-dimensional separation system for proteins," Journal of Chromatography B: Biomedical Sciences & Applications, 817(1):119-126 (2005).

Michels, D. A. et al., "Imaged capillary isoelectric focusing for charge-variant analysis of biopharmaceuticals," BioProcess International, 9(10):48-54 (Nov. 2011).

Misiakos et al., "A Multi-Band Capillary Immunosensor," Biosensors & Bioelectronics, 13:825-830 (1998).

Muller, O. et al., "Design of a high-precision fraction collector for capillary electrophoresis," Anal. Chem., 67(17):2974-2980 (1995).

Narang et al., "Multianalyte Detection Using a Capillary-Based Flow Immunosensor," Anal. Biochem., 225:13-19 (1998).

O'Neill, R. A. et al., "Isoelectric Focusing Technology Quantifies Protein Signaling in 25 Cells," PNAS, 103:16153-16158 (2006).

Rocklin, R. D. et al., "A microfabricated fluidic device for performing two-dimensional liquid-phase separations," Anal. Chem., 72(21):5244-5249 (2000).

Shang, T. Q., "Carrier ampholyte-free solution isoelectric focusing as a prefractionation method for the proteomic analysis of complex protein mixtures," Electrophoresis, 24:2359-2368 (2003).

Sosic, Z. et al., "Application of imaging capillary IEF for characterization and quantitative analysis of recombinant protein charge heterogeneity," Electrophoresis, 29(21):4368-4376 (Nov. 2008).

Vilkner, T. et al., "Micro Total Analysis Systems. Recent Developments," Analytical Chemistry, 76(12):3373-3385 (2004).

Wakankar, A. et al., "Analytical methods for physicochemical characterization of antibody drug conjugates," Landes Bioscience, 3(2):161-172 (2011).

Wang et al., "Enhancement of the Sensitivity of a Capillary Electrophoresis Immunoassay for Estradiol with Laser-Induced Fluorescence Based on a Fluorescein-labeled Secondary Antibody," Anal. Chem., 2001, 73:5616-5619.

Wu, J. et al., "Capillary isoelectric focusing with whole column detection and a membrane sample preparation system," Analytica Chimica Acta, 383(1-2):67-78 (1999).

Zhu, Z. et al., "Protein separation by capillary gel electrophoresis: a review," Analytica Chimica Acta, 709:21-31 (Oct. 2011).

* cited by examiner

METHOD TO PERFORM LIMITED TWO DIMENSIONAL SEPARATION OF PROTEINS AND OTHER BIOLOGICALS

RELATED APPLICATION

This application claims priority to U.S. Provisional Patent Application No. 61/023,492 filed on Jan. 25, 2008, and entitled SIMPLIFIED METHOD AND APPARATUS FOR CARRYING OUT LIMITED TWO DIMENSIONAL SEPARATION OF PROTEINS AND OTHER BIOLOGICALS, the disclosure of which is incorporated herein by reference.

BACKGROUND OF THE INVENTION

The present invention is in the technical field of two-dimensional separation of proteins and other biologicals and relates particularly to apparatus and a method for the rapid and reproducible separation of species in a liquid medium.

The separation and characterization of proteins is ubiquitous throughout the life sciences. Two of the most popular electrophoresis separation techniques are: 1) gel isoelectric focusing (IEF), where the separation mechanism is based on protein surface charge providing isoelectric point (pI) separation and 2) sodium dodecyl sulfate (SDS) gel electrophoresis where the separation mechanism is based on molecular weight (MW). These two techniques are most commonly performed individually.

Isoelectric focusing (IEF) is a special electrophoretic technique for separating amphoteric substances such as peptides and proteins in an electric field, across which there is both voltage and a pH gradient, acidic in the region of the anode and alkaline near the cathode. Each substance in the mixture will migrate to a position in the separation column where the surrounding pH corresponds to its isoelectric point. There, in zwitterion form with no net charge, molecules of that substance cease to move in the electric field. Different amphorteric substances are thereby focused into narrow stationary bands.

In IEF separation, it is well known that proteins having molecular weight differences or conformational differences may possess similar pI values and therefore focus at the same location. In order to then separate these co-focused proteins, a technique called two-dimensional (2D) gel electrophoresis has been employed. 2D gel electrophoresis combines two orthogonal separation techniques—gel IEF and SDS gel—to create a technique that dramatically increases separation resolution and provides for the separation of co-focused IEF protein zones. 2D gel electrophoresis is generally carried out in a polyacrylamide slab gel and although it has become a workhorse in the field of proteomics, owing to the high degree of resolution which can be obtained thereby, it is very labour-intensive, time consuming and non-quantitative.

Moreover, although 2D gel electrophoresis does afford the highest degree of molecular weight resolution of known electrophoretic separation techniques, it has not yet been possible to automate that process nor quantify the resolved component proteins or other analytes. These and other drawbacks have motivated researchers to combine two orthogonal separation techniques in the liquid phase, using a capillary or coplanar microchannel format. While these are necessarily "limited resolution" techniques, relative to 2D gel electrophoresis, they are much simpler and faster to use and are of adequate resolution for many purposes.

It is known to combine capillary or channel isoelectric focusing (cIEF) with non-porous reverse phase microliquid chromatography (RPLC) in a two-dimensional layout, to obtain useful online detection and quantitation. However, the interface between the first and second separation dimension has hitherto been carried out only at the outlet end of the IEF separation capillary or channel. It is known that the separation and pH gradient obtained in cIEF may be disturbed when mobilizing focused protein zones to reach the outlet end. A as result, it is more challenging to transfer separated zones from the first separation dimension to the second separation dimension in the orthogonal capillary or microchannel format than in apparatus for 2D gel electrophoresis. Fluid connections and for control of nanoliter volumes are required, making for complex analytical design and operation.

BRIEF SUMMARY OF THE INVENTION

This invention describes improved method and apparatus for carrying out limited electrophoretic separation in the liquid phase. The objective of the invention is to provide a simple method and apparatus for limited "2D" separation using both capillary or channel IEF separation and capillary zone electrophoresis (CZE) separation within the same capillary or channel. The present invention also integrates real-time, whole-channel electrophoresis detection with automatic sample injection, automatic cIEF separation, separation zone manipulation and on-line electrolyte selection, to achieve a separation resolution superior to that obtained using an orthogonal capillary arrangement.

The quotation marks about "2D" above reflect the fact that the present invention uses two different and sequential electrophoretic techniques, but not orthogonal capillaries as in the known arrangements described above. The term "2D" is, a convenient shorthand term for designating a method and apparatus employing two-stage electrophoretic separation, and will be used in the remainder of the specification and in the claims without quotation marks.

DETAILED DESCRIPTION OF THE INVENTION

Figure 1:
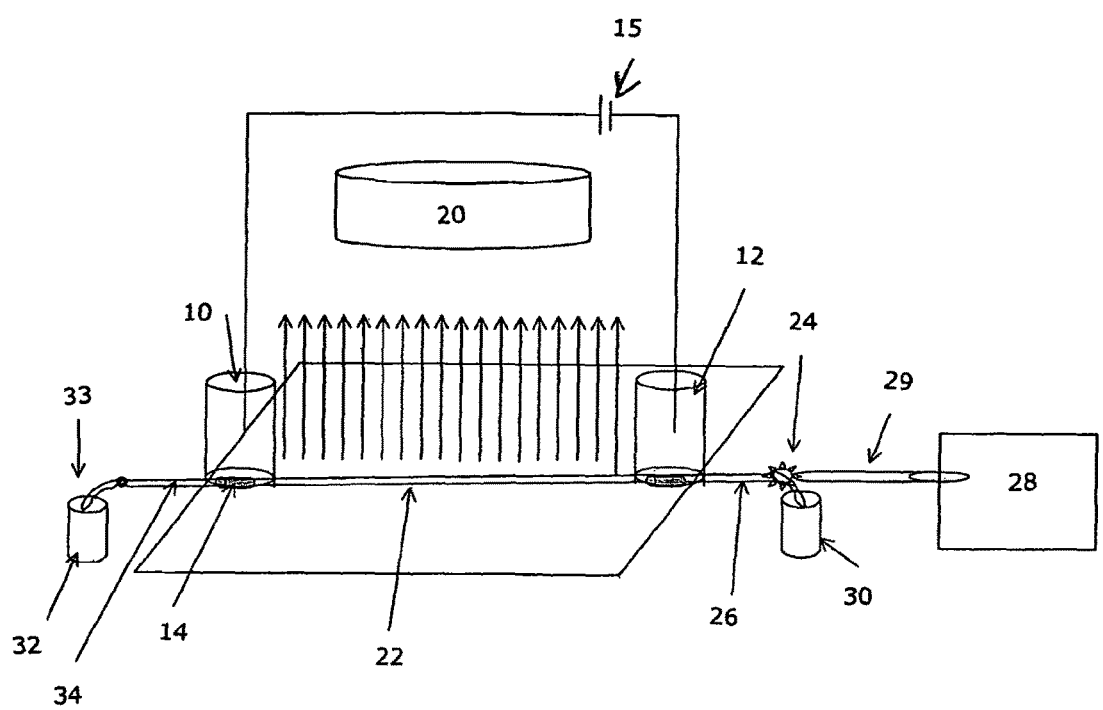
FIG. 1 is a schematic representation of a first embodiment of apparatus for performing limited 2D separation using electrophoresis and controlled hydrodynamic flow.

FIG. 1 shows a first embodiment of the apparatus. A microfluid device is provided, including an anolyte tank 10 and a catholyte tank 12 such that electrolyes in the tanks are isolated from the sample mixture by ion conductive barriers 14 (such as semipereamble membranes). A high voltage supply connected across two electrodes that are immersed in the respective tanks. A CCD imaging camera 20 is focused so that it can detect light passing through or emitted from the entire length of a horizontal capillary separation channel 22. The camera 20 is able to display and capture pictures in real-time, or at least very rapidly. A light source and collimation means (not shown) are provided for applying a sheet of light (arrows L) to pass through or emit from the entire length of separation channel 22. A real time CCD sensor camera/sensor arrangement like that used with the apparatus of the present invention is described in more detail in U.S. Pat. No. 6,852,206, having a common inventor and the same assignee as the present application. U.S. Pat. No. 6,852,206 is hereby incorporated by reference for its disclosure of detection and measurement apparatus of analyte separation zones in a capillary.

A switch valve 24 is connected to the microfluidic device such that an inlet flow channel portion 26 at one end of the separation channel may be selectively connected to either an autosampler 28 for sample injection, or to the fluid medium contents of an inlet vial 30. A hydrodynamic flow across separation channel 22 can be induced and controlled by vertical up or down fine-control motion of a hydrodynamic flow vial 32 containing fluid medium, the contents of which are connected by means of hydrodynamic flow control valve 33 with an outlet flow channel portion 34 of the separation channel.

With the switch valve 24 position set for fluid connection of the inlet channel portion 26 of the separation channel to the autosampler 28, and with a shut-off valve for autosampler connection tube 29 open, a sample containing a mixture of proteins, carrier ampholytes and a sieving solution such as methyl cellulose is injected into the separation channel by the autosampler until the sample mixture volume fills the separation channel to overflow. The position of the switch valve is then set to connect the inlet vial with the separation channel and the high voltage is turned on by means of HV switch 36. An electric field is thereby established across the separation channel and a linear pH gradient is formed by the carrier ampholytes. The cIEF process begins and upon completion, proteins are focused and separated into zones according to their pI when both electro-osmotic flow and hydrodynamic flow are stable. The entire IEF process is continuously monitored and the images of the separation trace are continuously captured (recorded) in real-time by the whole-channel CCD imaging camera of the CCD sensor unit. At this point, the first dimensional separation (cIEF) is complete and the second dimensional separation is initiated.

Figure 2:
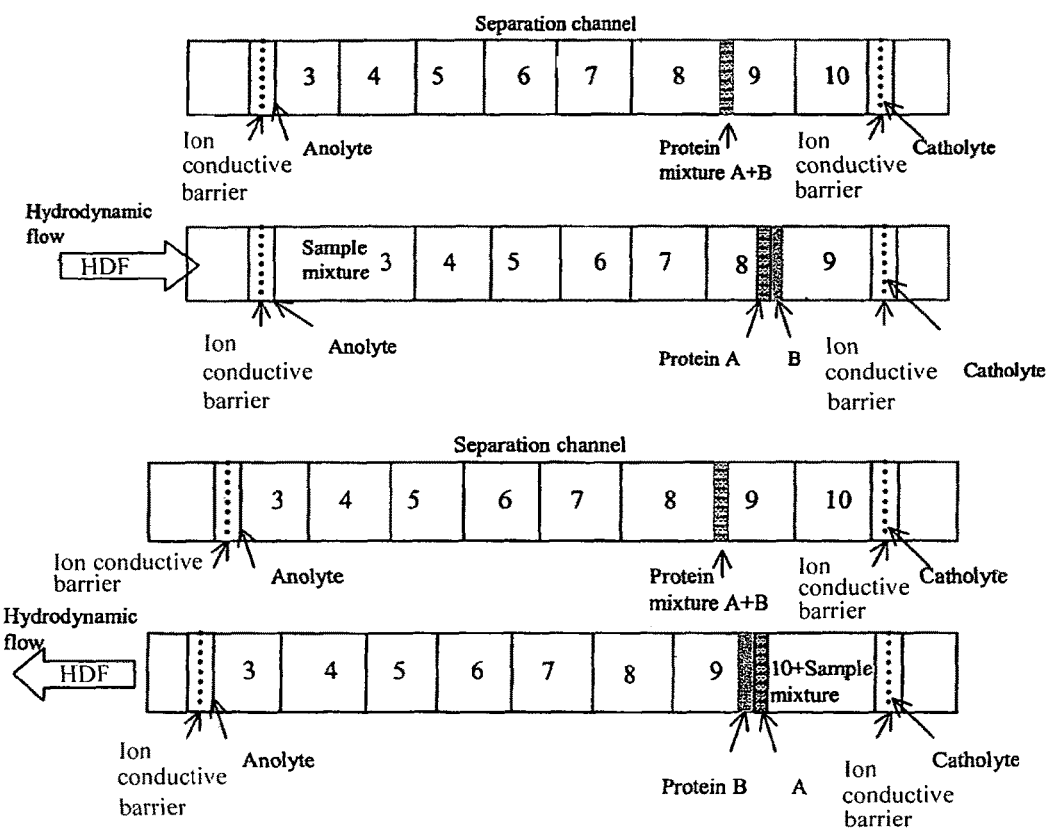
FIG. 2 illustrates schematically a physiochemical mechanism postulated to explain the separation of proteins in the presence of a hydrodynamic flow as in the method of the invention.

The second dimensional separation is applied to the IEF focused zones (proteins) by the application of a controlled hydrodynamic flow. The hydrodynamic flow is induced by a microgravitational force arising in the separation channel 22 resulting from the finely controlled up or down motion of the hydrodynamic flow vial. When hydrodynamic flow is introduced into the separation channel following IEF focusing, the pH gradient will be affected and additional sample mixture will enter the separation channel. As more sample mixture is continuously injected into the separation channel owing to the hydrodynamic flow, the focused zones at the far end of the separation channel (along the direction of hydrodynamic flow) are continuously pushed out. For example, if the outlet vial 32 is raised slightly, then the hydrodynamic flow direction proceeds from the anodic (outlet end) to the cathodic end (inlet end). More sample mixture is introduced from the anodic end, and the most basic zones focused at the cathodic end will be pushed out of the separation capillary (over the ion conductive barrier area, see FIG. 2). Since this hydrodynamic flow coexists with an electric field, the separation zone resolution and shape is preserved when the hydrodynamic flow is limited and carefully controlled and the newly injected sample mixture ampholytes are focused into their pI position. The movement of relatively larger molecular weight proteins (protein A in FIG. 2) is slower than that of smaller ones (protein B in FIG. 2) in a sieving solution such as methylcellulose. As a result, a limited second dimensional separation of cIEF zones (proteins) due to mass difference is achieved. Again, the entire second dimension separation process is continuously monitored and the images of the separation trace are continuously captured (recorded) in real-time by the whole-channel, CCD imaging camera.

Figure 3:
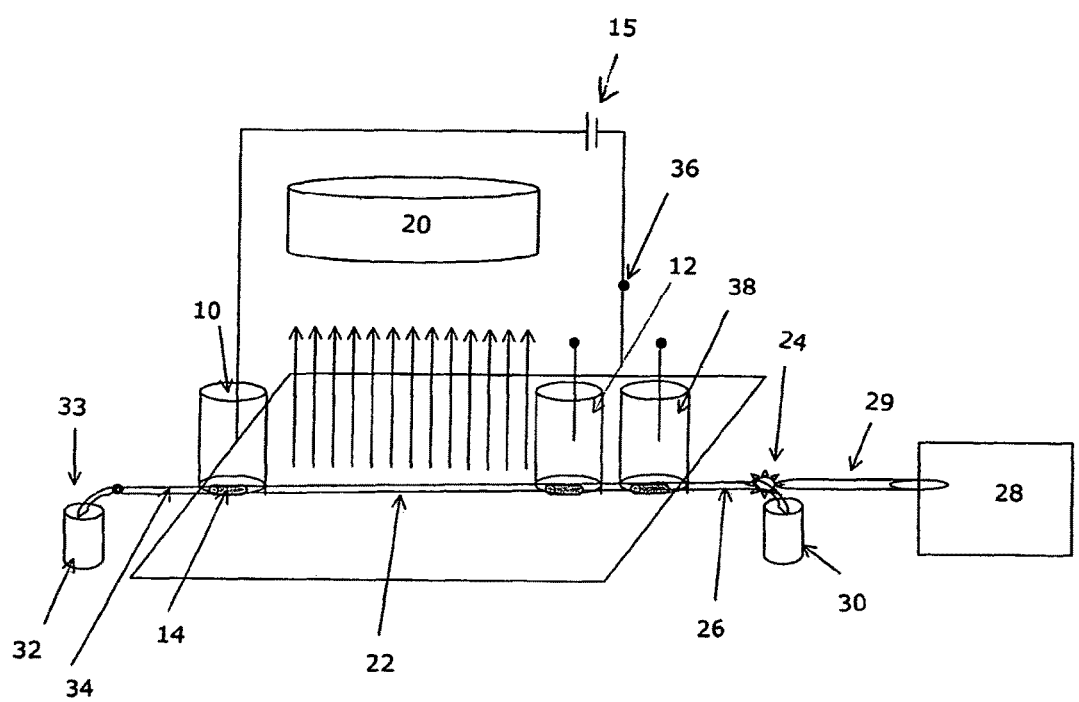
FIG. 3 is a schematic representation of a second embodiment of apparatus according to the invention for performing limited 2D separation using electrophoresis and chemical mobilization.

FIG. 3 shows a second embodiment of the apparatus. The same reference numerals are used to indicate components corresponding to those of the first apparatus embodiment (FIG. 1). The microfluid device contains an analyte tank 10, a catholyte tank 12 and a chemical mobilization tank 38. The electrolyes in the three tanks are isolated from the sample mixture by ion conductive barriers 14. High voltage supply is connected at one end to an electrode immersed in the anolyte tank and at the other end to HV switch 36 such that connection can be made to either an electrode immersed in the catholyte tank or an electrode immersed in the chemical mobilization tank. Real time CCD sensor 20 is focused such that it can detect light (arrows L) passing through or emitted from the entire length of separation channel 22 and the camera is able to display and capture pictures in real-time, or at least very rapidly. Means (not shown) are provided in both the first and second embodiments of the invention for projecting a sheet of light to pass through or emit from the entire length of the separation channel. As with the first embodiment described above switch valve 24 is connected to the microfluidic device such that the inlet flow channel 26 may be connected to either autosampler 18 for sample injection or to an inlet vial 30. The end of the outlet channel is immersed in an outlet vial.

The anolyte, catholyte and chemical mobilization tanks (10, 12, 38) are filled with appropriate electrolytes and, with the switch valve position set for connection between the inlet of the separation channel and the autosampler and the shut-off valve to capillary section 29 open, a sample containing a mixture of proteins, carrier ampholytes and a sieving solution such as methyl cellulose solution is injected into the separation channel by the autosampler until the sample mixture volume fills the separation channel to overflow. The switch valve position is then set for connection between inlet vial 30 and separation channel 22, the high voltage is turned on and the switch valve 24 is set such that the catholyte electrode is contacted, an electric field established across the separation channel, and a linear pH gradient is formed by the carrier ampholytes. The cIEF process begins and upon completion, proteins are focused and separated into zones according to their pI when both electro-osmotic flow and hydrodynamic flow are well controlled.

The entire cIEF process is continuously monitored and the images of the separation trace are continuously captured (recorded) in real-time by the whole-channel, CCD imaging camera. At this point, the first dimensional separation (cIEF) is complete and the second dimensional separation begins.

The second dimensional separation is achieved in this second embodiment of the apparatus, not by controlled hydrodynamic pressure but by chemical mobilization of the cIEF focused zones. An electric switch that is selectively operable to connect to anolyte electrode or the catholyte electrode is changed to connect to the chemical mobilization solution upon completion of cIEF. Mobilization of the focused zones will then occur. It is known that when non-acid solution is used as the anolyte, focused cIEF zones will migrate towards the anode (anodic mobilization). Whereas when non-base solution is used as the catholyte, focused cIEF zones will migrate towards the cathode (cathodic mobilization). Therefore, anodic mobilization may be achieved by switching the high voltage contact to the anode from the acid solution tank to the chemical mobilization tank that contains non-acid solution, or cathodic mobilization may be achieved by switching the high voltage contact to the cathode from the base solution tank to the chemical mobilization tank that contains non-base solution.

Figure 4:
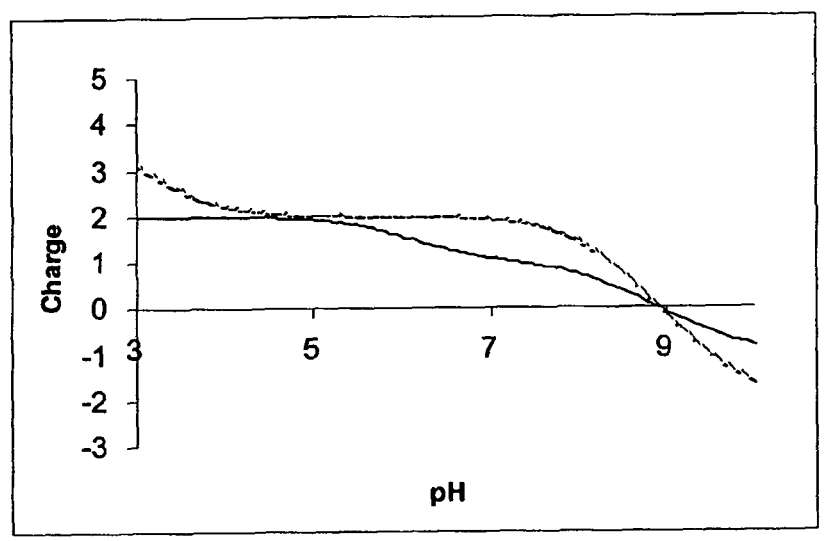
FIG. 4 illustrates graphically the separation of two proteins having the same pI value but different charge responses to pH, using the method of the invention.

The rate of migration due to chemical mobilization is determined by the charge-to-mass ratio of the protein and the mobility of the protein in a specific sieving solution. For example, two exemplary proteins with the same pI value have different rates of migration in response to a pH change (FIG. 4). As a result, these two proteins will not experience the same rate of motion during chemical mobilization. In addition, when this movement is carried out in a sieving solution, proteins with different molecular weight or shape (conformation) may have different mobility. Therefore, proteins with the same pI, but have different mobility change with pH or different molecular weights or conformation can be separated with limited 2D separation of cIEF zones using chemical mobilization. Again, the entire second dimension separation process is continuously monitored and the images of the separation trace are continuously captured (recorded) in real-time by the whole-channel, CCD imaging camera.

cIEF is a steady state technique. Focusing and separation of proteins is achieved when transitional peaks or zones converge into stationary zones. However, if single-point detection is used, it is difficult to know the exact time when all proteins are focused, since the speed of protein focusing is affected by sample conditions such as: content of salt and carrier ampholytes in the sample, experimental conditions such as separation channel dimensions, electric field strength and electrolyte concentration. As a result, two transitional peaks or zones for one protein may be detected when the protein is not yet focused. Further, an abnormal peak may be observed due to protein aggregation or precipitation resulting from prolonged protein focusing. With whole-column detection, as used with the present invention, however, the separation and focusing of an individual protein can be monitored in real time, avoiding the problems of 2D separation of transitional peaks (premature focusing) and separation of precipitated proteins (over focusing). The pI value of the protein is calibrated and the second dimension separation is applied. With real-time, whole column detection, the protein separation can be monitored, providing better protein fingerprinting by allowing straightforward assignment of protein zones based on pI and relative molecular weight differences.

EXAMPLE 1:

Induced Hydrodynamic Flow as Second Dimension of Separation

Figure 5:
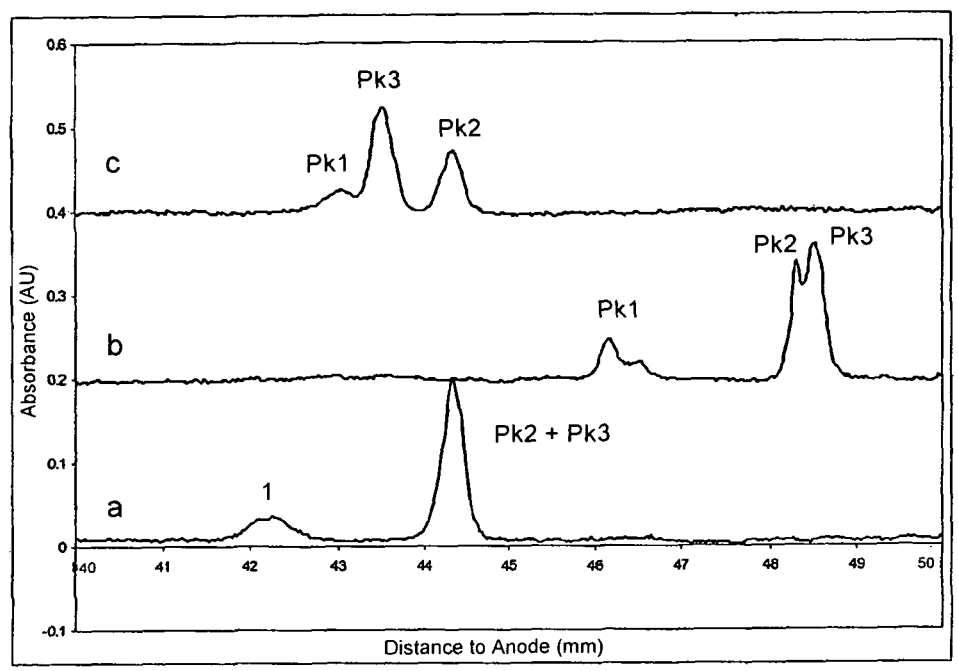
FIG. 5 illustrates graphically the results of a separation effected by using apparatus according to the first embodiment of the invention, showing a single peak of tryptosinogen and pI Marker 9.46 mixture when hydrodynamic flow is minimized, and split peak of tryptosinogen and pI Marker 9.46 when hydrodynamic flow is toward the cathode.

FIG. 5 illustrates hydrodynamic flow induced limited 2D separation of protein trypsinogen and a small molecular weight pI marker. In this experiment, trypsinogen and a small molecular pI marker were mixed with 8% pH 3-10 Pharmalyte and 0.35% methylcellulose. The sample mixture was injected into a 50 mm 100 µm inner diameter FC coated capillary with a micro autosampler. Focusing was conducted at a focusing voltage of 3000 V, with 80 mM $H_3PO_4$ as anolyte and 100 mM NaOH as catholyte. Detection was conducted with a real-time, whole column UV detector. The hydrodynamic flow is controlled by the water level difference in the hydrodynamic flow vial and the inlet vial.

It can be seen that when hydrodynamic flow was minimized (i.e. under first dimension cIEF separation conditions), there were two peaks in the electrophorogram (trace a). The more acidic peak to the left of the electrophorogram (egram) contains the minor component of trypsinogen (pk 1) and the more basic peak to the right of the egram contains the major component of trypsinogen (pk 2) and the pI marker (pk 3). When a hydrodynamic flow was introduced in the direction of the cathodic end (trace b), the minor component of trypsinogen (pk 1) further partially separated into two subcomponents, and the pI marker (pk 3) was partially separated from peak the major component of trypsinogen (pk 2). The pI marker (pk 3) moved more quickly to a more basic position than the major trypsinogen component (pk 2) due to its smaller molecular weight in a sieving solution. When a hydrodynamic flow was introduced in the direction of the anodic end (trace c), again because of the smaller MW of the pI marker (pk 3) compared to that of the major component of trypsinogen (pk 2), the pI marker shifted more quickly to a more acidic position than that of the major component of trypsinogen.

EXAMPLE 2:

Chemical Mobilization as Second Dimension of Separation

Figure 6:
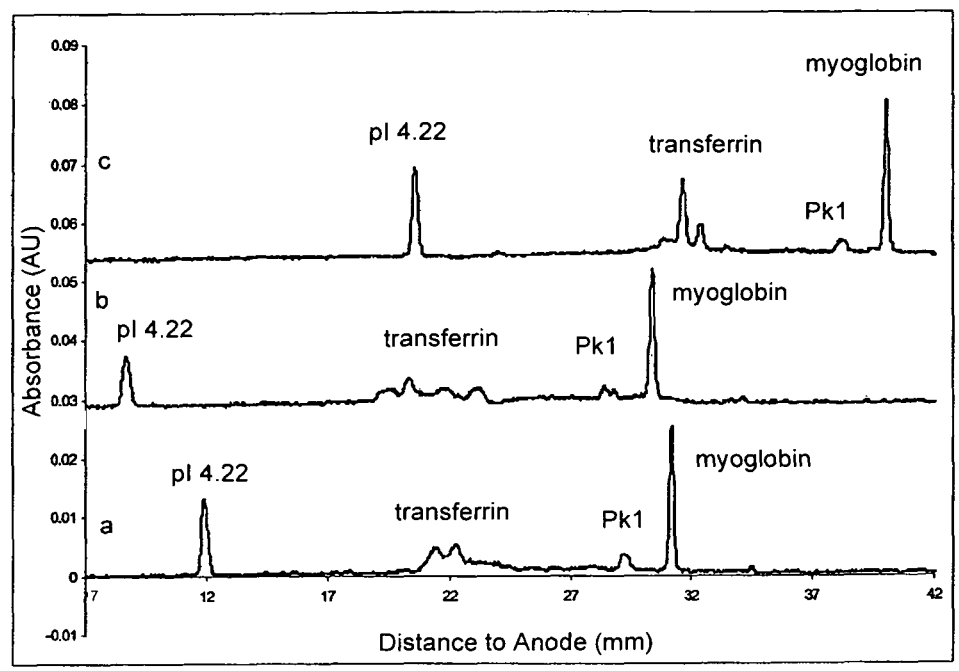
FIG. 6 illustrates graphically the results of a separation effected by apparatus according to the second embodiment of the invention, showing two peaks of transferrin prior to anodic mobilization and four peaks of transferring subsequent to anodic chemical mobilization.

FIG. 6 illustrates chemical mobilization induced limited 2D separation of transferrin, myoglobin and a small molecular weight pI marker (pI 4.22). In this experiment, transferrin and myoglobin and the pI marker were mixed with 8% pH 3-10 Pharmalyte and 0.35% methylcellulose. The sample mixture was injected into a 50 mm 100 µm inner diameter FC coated capillary with a micro autosampler. Focusing was conducted at a focusing voltage of 3000 V, with 80 mM $H_3PO_4$ as anolyte and 100 mM NaOH as catholyte. Detection was conducted with a real-time, whole column UV detector. For anodic mobilization (trace b), the anolyte was replaced with 100 mM NaOH upon completion of cIEF focusing. For cathodic mobilization (trace c), the catholyte was replaced with 80 mM $H_3PO_4$ upon completion of focusing. In Trace a, it can be seen that when electroosmotic flow and hydrodynamic flow are well controlled (i.e. under first dimension cIEF separation conditions), the transferrin protein is partially resolved into two peaks and a minor myoglobin peak (pk 1) is noted. Under anodic mobilization (trace b), the transferrin protein is now partially resolved into 4 peaks and the minor myoglobin component is partially resolved into 2peaks (pk 1). When cathodic chemical mobilization was introduced (trace c), the two peaks of transferrin (trace a) are separated into two larger peaks and one smaller peak.

Neither chemical mobilization conditions produced any split or partially separation of the pI marker peak (pI 4.22) and the major myoglobin peak.

CONCLUSION

From the description and examples herein it will be seen that applicants' provides a rapid, reproducible and quantative limited 2D electrophoresis separation. Channel or capillary-based electrophoresis, unlike 2D gel electrophoresis permits automatic sample injection. No sample transfer or handling is involved and either hydrodynamic flow or chemical mobilization can be used, since both can be well controlled. Applicants' arrangement allows "two-dimensional" electrophoresis to be carried out within a single separation channel and in a single analysis run. The use of real time, whole channel image detection affords very good reproducibility in both qualitative and quantative characterization.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

We claim:

1. A method, comprising:
   loading an inlet reservoir and a separation channel of an electrophoretic cell with a solution including a plurality of proteins, an amphoteric carrier medium, and a sieving solution, the inlet reservoir fluidically coupled to the separation channel;
   during a first separation stage:
      establishing a pH gradient across the separation channel, the pH gradient being static during the first separation stage;
      applying a voltage to the separation channel in the presence of the pH gradient such that the plurality of proteins are focused into a zone having a pH value corresponding to a pI value of each protein from the plurality of proteins in that zone, the zone being static during the first separation stage;
   during a second separation stage mutually exclusive from the first separation stage:
      drawing the sample from the inlet reservoir into the separation channel inducing a hydrodynamic flow within the separation channel causing the zone to move away from the inlet reservoir such that each protein from the plurality of proteins is displaced from the pH value corresponding to the pI value of each protein from the plurality of proteins and such that each protein from the plurality of proteins moves towards the zone effecting a separation of the plurality of proteins by mobility; and
      continuously monitoring the plurality of proteins during the second separation stage using a whole column imaging detector; and
      detecting a separation of a first protein from a second protein during the second separation stage due to the first protein having a different mobility than the second protein, the first protein and the second protein each being from the plurality of proteins.

2. The method of claim 1, wherein the plurality of proteins are a first plurality of proteins, the pI value is a first pI value, and the sample includes a second plurality of proteins having a plurality of pI values different from the first pI value.

3. The method of claim 1 wherein the first separation stage concludes when the plurality of proteins are focused into the zone.

4. The method of claim 1, further comprising:
   continuously monitoring the plurality of proteins during the first separation stage using the whole column imaging detector, the hydrodynamic flow induced in response to the whole column imaging detector detecting that each protein from the plurality of proteins is focused into the zone.

5. The method of claim 1, wherein the first protein has a first mobility and the second protein has a second mobility greater than the first mobility such that the second protein moves through the sieving solution towards the zone during the second separation stage faster than the first protein.

6. The method of claim 1, wherein the plurality of proteins are focused during the first separation stage via isoelectric focusing.

7. The method of claim 1, wherein the monitoring includes monitoring along substantially an entire length of the separation channel simultaneously.

8. The method of claim 1, wherein the sieving solution is methyl cellulose.

9. The method of claim 1, wherein:
   the plurality of proteins is a first plurality of proteins;
   the zone is a first zone having a first pH value corresponding to a first pI value of each protein from the first plurality of proteins;
   the solution includes a second plurality of proteins;
   during the first separation stage the voltage is applied to the separation channel such that a first plurality of protein are focused into the first zone and such that a second plurality of proteins are focused into a second zone having a second pH value corresponding to a second pI value of each protein from the second plurality of proteins; and
   the first zone and the second zone are static during the first separation stage.

10. The method of claim 1, wherein:
   the plurality of proteins is a first plurality of proteins;
   the zone is a first zone having a first pH value corresponding to a first pI value of each protein from the first plurality of proteins;
   the solution includes a second plurality of proteins;
   during the first separation stage the voltage is applied to the separation channel such that a first plurality of protein are focused into the first zone and such that a second plurality of proteins are focused into a second zone having a second pH value corresponding to a second pI value of each protein from the second plurality of proteins;
   during the second separation stage the hydrodynamic flow causes the first zone to move away from the inlet reservoir such that each protein from the first plurality of proteins is displaced from the first pH value corresponding to the first pI value such that each protein from the first plurality of proteins moves towards the first zone effecting a separation of the first plurality of proteins by mobility; and during the second separation stage the hydrodynamic flow causes the second zone to move away from the inlet reservoir such that each protein from the second plurality of proteins is displaced from the second pH value corresponding to the second pI value such that each protein from the second plurality of proteins moves towards the second zone effecting a separation of the second plurality of proteins by mobility.

11. A method, comprising:
loading a separation channel having a first end and a second end with a solution including a plurality of proteins, an amphoteric carrier medium, and a sieving solution;
during a first separation stage:
   ionically coupling a first anolyte reservoir containing an acid to the first end of the separation channel and a first catholyte reservoir containing a base to the second end of the separation channel such that a first pH gradient is established across a length of the separation channel, the first pH gradient being static during the first separation stage;
   applying a voltage to the separation channel in the presence of the first pH gradient such that the plurality of proteins are focused into a zone having a pH value corresponding to a pI value of each protein from the plurality of proteins in that zone, the zone being static during the first separation stage;
during a second separation stage mutually exclusive from the first separation stage:
   ionically coupling at least one of a second anolyte reservoir different from the first anolyte reservoir to the first end of the separation channel or a second catholyte reservoir different from the first catholyte reservoir to a second end of the separation channel, such that the at least one of the second anolyte reservoir or the second catholyte reservoir replaces at least one of the first analyte reservoir or the first catholyte reservoir such that a second pH gradient different from the first pH gradient is established across the length of the separation channel and such that each protein from the plurality of proteins is displaced from the pH value corresponding to the pI value of each protein from the plurality of proteins and such that each protein from the plurality of proteins moves towards the zone effecting a separation of the plurality of proteins by mobility; and
   continuously monitoring the plurality of proteins during the second separation stage using a whole column imaging detector.

12. The method of claim 11, wherein each protein from the plurality of proteins has the pI value.

13. The method of claim 11, wherein the plurality of proteins are a first plurality of proteins, the sample includes a second plurality of proteins.

14. The method of claim 11, wherein the second anolyte reservoir contains a non-acid.

15. The method of claim 11, wherein the second catholyte reservoir contains a non-base.

16. The method of claim 11, wherein the first separation stage concludes when the plurality of proteins are focused into the zone.

17. The method of claim 11, further comprising:
continuously monitoring the plurality of proteins during the first separation stage using the whole column imaging detector, the at least one of the second anolyte reservoir or the second catholyte reservoir ionically coupled to the separation channel in response to the whole column imaging detector detecting that each protein from the plurality of proteins is focused into the zone.

18. The method of claim 11, wherein:
the plurality of proteins includes a first subset of proteins having a first pI and a second subset of proteins having a second pI; and
during the first separation stage the voltage is applied to the separation channel such that the first subset of proteins are focused into a first zone having a first pH value corresponding to the first pI value and the second subset of proteins are focused into a second zone having a second pH value corresponding the second pI value.

19. The method of claim 11, further comprising:
detecting, via the continuous monitoring during the second separation stage, a first peak associated with a first protein from the plurality of proteins and a second peak associated with a second protein from the plurality of proteins, the first protein having a pI and a first mobility, the second protein having the pI and a second mobility different from the first mobility.

20. The method of claim 11, further comprising:
detecting, via the continuous monitoring during the second separation stage, a first peak associated with a first protein from the plurality of proteins, a second peak associated with a second protein from the plurality of proteins, a third peak associated with a third protein from the plurality of proteins, and a forth peak associated with a fourth protein from the plurality of proteins, the first protein having a first pI and a first mobility, the second protein having the first pI and a second mobility different from the first mobility, the third protein having a second pI different from the first pI and a third mobility, the fourth protein having the second pI and a fourth mobility different from the third mobility.

* * * * *